(12) United States Patent
Chahal et al.

(10) Patent No.: US 9,421,159 B2
(45) Date of Patent: Aug. 23, 2016

(54) PROTEIN-ACRYLATE COPOLYMER AND HAIR CONDITIONING PRODUCT COMPRISING SAID POLYMER

(75) Inventors: Surinder Pall Chahal, Warrington (GB); Ian Robert Tooley, Warrington (GB); Neil Howard James, Chester (GB); Charlotte Odette Camille Stricane, Liverpool (GB)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 13/634,662

(22) PCT Filed: Mar. 25, 2011

(86) PCT No.: PCT/GB2011/000435
§ 371 (c)(1),
(2), (4) Date: Sep. 13, 2012

(87) PCT Pub. No.: WO2011/121279
PCT Pub. Date: Oct. 6, 2011

(65) Prior Publication Data
US 2013/0004450 A1 Jan. 3, 2013

(30) Foreign Application Priority Data
Mar. 30, 2010 (GB) .................................. 1005382.5

(51) Int. Cl.
A61K 8/02 (2006.01)
A61K 8/81 (2006.01)
A61Q 5/12 (2006.01)
C08F 289/00 (2006.01)

(52) U.S. Cl.
CPC ................ *A61K 8/8152* (2013.01); *A61Q 5/12* (2013.01); *C08F 289/00* (2013.01)

(58) Field of Classification Search
None
See application file for complete search history.

(56) References Cited

U.S. PATENT DOCUMENTS

| 3,359,222 A | 12/1967 | Faessinger et al. |
| 3,711,574 A | 1/1973 | Jaworek et al. |
| 4,283,384 A * | 8/1981 | Jacquet et al. ................ 424/47 |
| 4,388,428 A | 6/1983 | Kuzma et al. |
| 4,478,976 A | 10/1984 | Goertz et al. |
| 4,940,663 A | 7/1990 | Eyssautier |
| 5,714,560 A | 2/1998 | Denzinger et al. |
| 2005/0050656 A1* | 3/2005 | Huang et al. .................... 8/406 |
| 2006/0280710 A1 | 12/2006 | Wong et al. |
| 2007/0065387 A1* | 3/2007 | Beck et al. ................ 424/70.13 |

FOREIGN PATENT DOCUMENTS

| DE | 10238176 | 3/2004 |
| EP | 0172580 | 2/1986 |
| FR | 2327761 | 5/1977 |
| GB | 0943171 | 12/1963 |
| GB | 1407659 | 9/1975 |
| GB | 1541670 | 3/1979 |
| GB | 2137654 | 10/1984 |
| JP | 52-54034 | 5/1977 |
| JP | 61-141719 | 6/1986 |
| JP | H05092910 | 4/1993 |
| JP | 10-500440 | 1/1998 |
| WO | WO 2004/026927 | 4/2004 |
| WO | WO 2005/039641 | 5/2005 |

OTHER PUBLICATIONS van Dijk-Wolthuis et al., A Bersatile Method for the Conjugation of Proteins and Peptides to Poly[2-(dimethylamino)ethylmethacrylate], 1999, Bioconjugate Chem., vol. 10, pp. 687-692.*
International Search Report dated Jul. 15, 2011 for PCT/GB2011/000435.
Search Report prepared Jul. 30, 2010 for related priority British Application No. GB 1005382.5.
English translation of Examination Report mailed Aug. 12, 2014 in corresponding Japanese Application No. JP 2013-501926.
EP Examination Report dated Jul. 10, 2015 from corresponding European Application No. 11713501.2.

* cited by examiner

*Primary Examiner* — Nannette Holloman
(74) *Attorney, Agent, or Firm* — RatnerPrestia

(57) ABSTRACT

A protein-acrylate copolymer contains at least one nitrogen containing acrylic monomer. The nitrogen containing acrylic monomer preferably contains a tertiary or quaternary amine group, and particularly a quaternary amine group. The protein-acrylate copolymer can be produced by reacting hydrolyzed protein with at least one nitrogen containing acrylic monomer, preferably by free-radical polymerization. The protein-acrylate copolymer is suitable for use in personal care or cosmetic products, particularly in hair care products where it can increase volume to hair.

20 Claims, No Drawings

PROTEIN-ACRYLATE COPOLYMER AND HAIR CONDITIONING PRODUCT COMPRISING SAID POLYMER

CROSS REFERENCE TO RELATED APPLICATION

This application is the National Phase application of International Application No. PCT/GB2011/000435, filed Mar. 25, 2011, which designates the United States and was published in English. The foregoing related application, in its entirety, is incorporated herein by reference.

FIELD OF INVENTION

The present invention relates to a protein-acrylate copolymer, a personal care or cosmetic product comprising the copolymer, and in particular to a hair care product which adds volume to hair.

BACKGROUND

There is a continual requirement for improved hair care actives and end-use products containing such actives. One such product category which creates a fuller appearance or body for the hair is known as a hair volumiser. Some existing volumising products use fixative-based sprays, gels, or mousses to enhance styling and create volume. These products work by gluing hair together in a fixed architecture with increased volume. Such products often have the disadvantage of causing hair to be stiff or excessively sticky and do not generally allow the user to restyle the hair without washing out the product and reapplying it. The end-user desires a volumising product which is not a permanent wave product, fixative-based hair spray, or styling gel.

There is a need for a volumising effect to be obtained from the use of a wide range of hair care products such as a shampoo, conditioner, 2-in-1 shampoo/conditioner, spray, liquid rinse, gel, or mousse etc. In addition, such products are required to give effective volume without enhancing frizzing of the hair or encouraging fly-away hair. Ideally, a volumising active should be capable of being effective in a wide range of hair care products.

SUMMARY OF THE INVENTION

We have surprisingly discovered a protein-acrylate copolymer, and use thereof in hair care products, that overcomes or significantly reduces at least one of the aforementioned problems.

Accordingly, the present invention provides a protein-acrylate copolymer comprising at least one nitrogen containing acrylic monomer.

The invention also provides a protein-acrylate copolymer obtainable by reacting a protein component with an acrylate component comprising at least one nitrogen containing acrylic monomer.

The invention further provides a composition comprising in the range from 0.01 to 20% by weight of a protein-acrylate copolymer, said copolymer comprising at least one nitrogen containing acrylic monomer.

The invention still further provides a method of producing a protein-acrylate copolymer which comprises reacting protein with at least one nitrogen containing acrylic monomer, and/or oligomer and/or polymer formed from at least one nitrogen containing acrylic monomer.

The invention yet further provides a method of treating hair by applying thereto a composition comprising a protein-acrylate copolymer, said copolymer comprising at least one nitrogen containing acrylic monomer.

The invention even further provides the use of a protein-acrylate copolymer for increasing the volume of hair, said copolymer comprising at least one nitrogen containing acrylic monomer.

The protein component starting material which is used to form the protein-acrylate copolymer of the present invention may be derived from either animal or vegetable sources, or by fermentation. Examples of proteins which are currently used in cosmetic formulations, and which can be used as the protein component of the copolymer, include collagen, elastin, keratin, casein, wheat protein, potato protein, soya protein, and/or silk protein. Wheat protein and/or potato protein are particularly preferred, and especially wheat protein.

The term "protein" is used herein to include both native (or chemically unmodified) and hydrolysed proteins, and thus comprises proteins properly so-called and polypeptides, peptides, amino acids and/or peptones, since the latter can all be categorised as hydrolysed proteins. Hydrolysed proteins are preferred, particularly polypeptides and peptides, which may for example be produced by acid, alkali, and/or enzyme hydrolysis, of native proteins. Enzyme hydrolysed proteins are preferred. In one embodiment, hydrolysed wheat proteins are preferred, in particular produced by enzyme hydrolysis.

Chemically modified proteins and/or hydrolysed proteins may also be employed, for example where the protein has been covalently reacted with a functional group, e.g. a silane, a quaternary ammonium compound and/or an acid chloride.

The molecular weight (weight average) of the protein component starting material may vary over a wide range, such as for example in the range from 100 to 500,000 Daltons.

In one embodiment, the molecular weight (weight average) of the protein component starting material is suitably in the range from 100 to 20,000, preferably 500 to 10,000, more preferably 500 to 4,000, further preferably 1,000 to 4,000, particularly 1,200 to 2,000, and especially 1,400 to 1,600 Daltons.

In an alternative embodiment, the molecular weight (weight average) of the protein component starting material is suitably in the range from 10,000 to 500,000, preferably 30,000 to 200,000, more preferably 50,000 to 150,000, particularly 60,000 to 100,000, and especially 70,000 to 90,000 Daltons.

One suitable hydrolysed protein or polypeptide comprises on average in the range from 2 to 200, preferably 5 to 100, more preferably 8 to 50, particularly 10 to 25, and especially 12 to 18 amino acids.

The composition of the amino acids in the protein component can also be an important parameter, and in one embodiment the protein comprises at least 1%, preferably in the range from 2 to 25%, more preferably 3 to 15%, particularly 4 to 10%, and especially 6 to 8% w/w of basic amino acids. The basic amino acids will normally be arginine, lysine, and/or histidine.

It is preferred that the protein component is capable of forming a solution in water or other suitable solvent or co-solvent (such as alcohol, propylene glycol, glycerine or polyethylene glycol) in order to enable reaction with the acrylate component to occur.

The acrylate component of the protein-acrylate copolymer of the present invention is formed from, or comprises the reaction product of, at least one nitrogen containing acrylic monomer. The monomer may comprise more than one nitrogen atom, but generally will comprise only one nitrogen atom. The nitrogen atom(s) is preferably part of an amine group. The amine group may be a primary, secondary, tertiary, and/or quaternary group. Preferably the amine group is a tertiary or quaternary, and particularly a quaternary amine group. Acrylic monomer, oligomer, and/or polymer may be reacted with the protein component in order to form the protein-acrylate copolymer. Quaternary acrylic monomer, oligomer, and/or polymer may be reacted with the protein component, or alternatively amine groups present in the copolymer may be quaternised in situ, i.e. after reaction of the protein component with the acrylate component.

The nitrogen containing acrylic monomer preferably comprises, consists essentially of, or consists of, (meth)acrylamide, a mono-, di- or tri-($C_1$-$C_4$)alkylamino ($C_1$-$C_4$)alkyl (meth)acrylate, a mono-, di- or tri-($C_1$-$C_4$) alkylamino($C_1$-$C_4$)alkyl(meth)acrylamide, and mixtures thereof.

The nitrogen containing acrylic monomer more preferably comprises, consists essentially of, or consists of, a dialkylaminoalkyl (meth)acrylate, a quaternised dialkylaminoalkyl (meth)acrylate, an acid addition salt of a quaternised dialkylaminoalkyl (meth)acrylate, and mixtures thereof.

The nitrogen containing acrylic monomer may comprise, consist essentially of, or consist of, monomers selected from the group comprising N,N-dimethylamino ethyl methacrylate (DMAEMA), N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N-diethylamino propyl acrylamide, N,N-diethylamino propyl methacrylamide, N,N,N-trimethylamino ethyl methacrylate (DMAEMA-MC), N,N,N-triethylamino ethyl acrylate, N,N,N-triethylamino ethyl methacrylate, N,N,N-trimethylamino propyl acrylamide, N,N,N-trimethylamino propyl methacrylamide, N,N,N-triethylamino propyl acrylamide, N,N,N-triethylamino propyl methacrylamide, or mixtures thereof.

Particularly preferred nitrogen containing acrylic monomers comprise, consist essentially of, or consist of, monomers selected from the group comprising N,N,N-trimethylamino ethyl methacrylate (DMAEMA-MC), N,N,N-triethylamino ethyl acrylate, N,N,N-triethylamino ethyl methacrylate, N,N,N-trimethylamino propyl acrylamide, N,N,N-trimethylamino propyl methacrylamide, N,N,N-triethylamino propyl acrylamide, N,N,N-triethylamino propyl methacrylamide, or mixtures thereof. N,N,N-trimethylamino ethyl methacrylate is a preferred monomer.

The nitrogen containing acrylic monomer(s) suitably comprises at least 20, preferably at least 40, more preferably at least 60, particularly in the range from 80 to 100, and especially 90 to 100 mole % of monomers comprising tertiary and/or quaternary, preferably quaternary, amine groups.

In addition to the nitrogen containing acrylic monomers described herein, the acrylic component of the protein-acrylate copolymer of the invention may comprise one or more other acrylic monomers. Suitable acrylic monomers include acrylic acid and/or methacrylic acid, and/or esters thereof, especially an alkyl ester wherein the alkyl group contains up to 10, more preferably up to 6, carbon atoms. Suitable alkyl groups may be selected from methyl, ethyl, n-propyl, isopropyl, n-butyl, isobutyl, terbutyl, hexyl, 2-ethyl, hexyl, heptyl, and n-octyl. In one embodiment, mixtures of any two or more of the aforementioned monomers are employed, for example an alkyl acrylate (such as ethyl acrylate and/or butyl acrylate) in combination with an alkyl methacrylate (such as methyl methacrylate).

The acrylate component may also comprise other, preferably optional, additional monomers, in addition to the aforementioned acrylic acid or methacrylic acid or esters thereof. Suitable additional monomers may be selected from the group comprising acrylonitrile, methacrylonitrile, halo-substituted acrylonitrile, halo-substituted methacrylonitrile, hydroxyethyl methacrylate, glycidyl acrylate, glycidyl methacrylate, itaconic acid, itaconic anhydride, and half esters of itaconic acid.

The acrylate component of the protein-acrylate copolymer of the present invention suitably comprises at least 10, preferably at least 20, more preferably at least 30, particularly in the range from 40 to 100, and especially 50 to 100 mole % of nitrogen containing acrylic monomers. Alkyl acrylate and/or alkyl methacrylate may be present in the range from 0 to 90, preferably 0 to 50, more preferably 0 to 30, and particularly 0 to 10 mole %. Generally it is preferred that less than 10, more preferably less than 5, particularly less than 2, and especially 0 mole % of acidic acrylic monomers, e.g. acrylic acid and/or methacrylic acid, are present.

In one embodiment, the molar ratio of nitrogen containing acrylic monomers to acidic acrylic monomers in the protein-acrylate copolymer is preferably in the range from 0.1 to 10:1, more preferably 0.3 to 3:1, particularly 0.5 to 2:1, and especially 0.8 to 1.2:1. Alkyl acrylate and/or alkyl methacrylate may be present in such copolymers the range from 0 to 80, preferably 0 to 60, more preferably 0 to 40 and particularly 0 to 30 mole %.

The molecular weight (weight average) of the acrylate component starting material which is reacted with the protein component to form the protein-acrylate copolymer of the invention is suitably in the range from 60 to 500,000, preferably 100 to 100,000, more preferably 100 to 10,000, particularly 150 to 5,000, and especially 150 to 1,000 Daltons. Acrylic monomers are preferably reacted with the protein component to form the protein-acrylate copolymer.

The protein-acrylate copolymer of the present invention may be a random, graft, or block copolymer. The copolymer is preferably a graft or block copolymer, and more preferably a graft copolymer. Cross-linking of the protein chains may occur. In one embodiment, the preferred graft copolymer will have a protein backbone and acrylate side-chains or grafts. However, the terminal amino group of the protein will normally also have been reacted with the acrylate component, and for the present purposes this is also considered to be a side chain or graft. The graft copolymer suitably comprises on average in the range from 1 to 20, preferably 1 to 10, more preferably 1 to 5, particularly 1 to 3, and especially 1 to 2 acrylate side chains.

The protein-acrylate copolymer may be represented schematically as follows;

protein chain-X-polyacrylate wherein X is a linking group resulting from the reaction of the protein with the (poly)acrylate, and the part derived from the protein is preferably NH or S, particularly NH, and polyacrylate comprises in the range from 2 to 1,000, preferably 5 to 500, particularly 10 to 200, and especially 20 to 100 acrylic monomers.

In a preferred embodiment, the protein-acrylate copolymer comprises at least one monomer having the following structure;

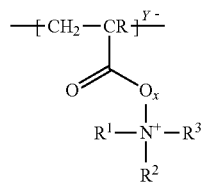

wherein R is H or CH$_3$, preferably CH$_3$,
x is 0 or 1, preferably 1,
R$^1$, R$^2$ and R$^3$ are independently C$_1$-C$_6$ alkyl, preferably methyl, ethyl, propyl or butyl, and particularly methyl,
Y$^-$ is a salt forming anion, preferably chloride, bromide, iodide, fluoride, sulphate, methyl sulphate, phosphate, nitrate or nitrite, and particularly chloride.

The protein-acrylate copolymer is suitably produced by reacting protein with one or more of the acrylic monomers described herein, preferably by free radical polymerisation as known in the art. Alternatively, oligomeric- and/or polyacrylates may be reacted with the protein, for example by converting some of the amine groups in the polyacrylate into protected thiols using N-succinimidyl 3-(2-pyridyldithio) propionate (SPDP). Following deprotection, the thiolated acrylate polymer can be conjugated to the protein via disulphide or thioether linkages.

Protein-acrylate copolymers may be produced by reacting protein with quaternary acrylic monomers, oligomers and/or polymers, or alternatively quaternisation can occur in situ, for example by reacting protein with tertiary amine acrylic monomers, oligomers and/or polymers and quaternising in situ for example with diethyl sulphate (e.g. in aqueous solution), dimethyl sulphate (e.g. in DMF), or alkyl and aryl halides such as methyl chloride, methyl iodide, methyl bromide, ethyl chloride, and benzyl chloride.

The ratio of protein component to acrylate component reacted together to form the protein-acrylate copolymer (or ratio of protein to acrylate present in the copolymer) is suitably in the range from 5%:95% to 95%:5%, preferably 20%:80% to 80%:20%, more preferably 30%:70% to 70%:30%, particularly 40%:60% to 60%:40%, and especially 45%:55% to 55%:45% by weight.

The molar ratio of nitrogen, preferably quaternary group, containing monomers in the acrylate component to amino groups in the protein component, which are reacted together to form the protein-acrylate copolymer (or molar ratio of nitrogen containing monomers to amino groups present in the copolymer), is preferably in the range from 0.1 to 10:1, more preferably 0.5 to 8:1, particularly 1 to 5:1, and especially 2 to 3:1.

The molecular weight (weight average) of the protein-acrylate copolymer of the present invention is suitably in the range from 2,000 to 1,000,000, preferably 20,000 to 500,000, more preferably 20,000 to 300,000, further preferably 50,000 to 300,000, particularly 100,000 to 200,000, and especially 125,000 to 175,000 Daltons.

In one embodiment, the unpurified or neat protein-acrylate copolymer reaction mixture, e.g. in the form of an aqueous solution, may be used to form a composition according to the present invention. By "neat" reaction mixture is meant without being subject to any separation or purification step (except for removal of any particulates, e.g. by filtration) after completion of the reaction, i.e. not removing any unreacted starting materials. The molecular weight (weight average) of the neat protein-acrylate copolymer reaction mixture is suitably in the range from 1,000 to 500,000, preferably 10,000 to 300,000, more preferably 20,000 to 100,000, particularly 40,000 to 70,000, and especially 50,000 to 60,000 Daltons.

The protein-acrylate copolymer reaction mixture is suitably in the form of an aqueous solution preferably comprising
(i) in the range from 5 to 50%, more preferably 10 to 40%, particularly 15 to 30%, and especially 17 to 25% by weight of solids (excluding salt) or active material based on the total weight of the solution, and
(ii) in the range from 50 to 95%, more preferably 60 to 90%, particularly 70 to 85%, and especially 75 to 83% by weight of water based on the total weight of the solution.

The aqueous solution may, for example, contain up to about 5%, normally up to about 2.5%, by weight of salt based on the total weight of the solution.

The protein-acrylate copolymer containing composition according to the present invention is preferably a personal care or cosmetic product, in particular a hair care or skin care, and especially hair care product. Typical personal care formulations include shampoos, hair colorants, hair conditioners, 2-in-1 shampoo/conditioners, bath products, skin treatment creams and lotions, body washes including facial washes, and wipes such as a cleansing wipes. Other formulations include make-up creams, sunscreens, skin-toners, antiperspirants, mascaras and the like. The composition is preferably a hair care product such as a shampoo, conditioner, 2-in-1 shampoo/conditioner, hairspray, hair spritz, hair colouring product, hair sunscreen product, styling mousse or gel, or other hair treatment composition.

The amount of protein-acrylate copolymer in the composition is suitably in the range from 0.01 to 20%, preferably 0.1 to 10%, more preferably 0.3 to 5%, particularly 0.4 to 2%, and especially 0.5 to 1%, by weight of said copolymer based on the total weight of the composition.

Typically, the composition according to the present invention comprises anionic, non-ionic, amphoteric, and/or cationic surfactants. In one embodiment, the composition comprises a protein-acrylate copolymer as described herein, in combination with at least one anionic surfactant.

Suitable anionic surfactants may be selected from the group comprising alkyl sulphates, alkyl ether sulphates, alpha olefin sulphonates, sulphosuccinates, isethionates, acyl amides, acyl glutamates, alkyl ether carboxylates, and alkyl phosphates. The alkyl group preferably comprises in the range from 6 to 30, more preferably 8 to 20, and particularly 10 to 14 carbon atoms. Alkyl sulphates are preferred, particularly sodium laureth sulphate. The concentration of anionic surfactant in the composition is suitably in the range from 0.5 to 25%, preferably 2 to 20%, more preferably 5 to 17%, particularly 8 to 14%, and especially 10 to 12% by weight based on the total weight of the composition.

The composition may also contain a secondary surfactant such as a nonionic, amphoteric, betaine, and/or cationic surfactant. The total concentration of anionic surfactant and secondary surfactant(s) in the composition is preferably in the range from 2 to 50%, more preferably 4 to 40%, particularly 6% to 30%, and especially 8% to 20% by weight based on the total weight of the composition.

Suitable nonionic surfactants may be selected from the group comprising fatty alcohol acid or amide ethoxylates, alkanolamides and alkoxylated alkanolamides, monoglyceride ethoxylates, sorbitan ester ethoxylates, and alkyl polyglycosides. The concentration of nonionic surfactant in the composition is preferably in the range from 0 to 30%, more preferably 0.5 to 20%, particularly 1 to 15%, and especially 2 to 10% by weight based on the total weight of the composition.

Suitable amphoteric surfactants may be selected from the group comprising alkylimino-diproprionates, alkylamphoglycinates, alkylamphoproprionates, alkylamphoacetates (mono- and di-), N-alkyl beta-aminoproprionic acids, alkylpolyamino carboxylates, and phosphorylated imidazolines. The concentration of amphoteric surfactant in the composition is preferably in the range from 0 to 20%, more preferably 0.5 to 15%, particularly 1 to 10%, and especially 2 to 8% by weight based on the total weight of the composition.

Suitable betaines may be selected from the group comprising alkyl betaines, alkylamido betaines, alkyl sultaines, and alkylamido sultaines. The alkyl group preferably has in the range from 6 to 30, more preferably 8 to 20, and particularly 10 to 14 carbon atoms. The concentration of betaine surfactant in the composition is preferably in the range from 0 to 20%, more preferably 1 to 15%, particularly 3 to 12%, and especially 7 to 10% by weight based on the total weight of the composition.

Suitable cationic surfactants may be selected from the group comprising alkyl quaternaries, benzyl quaternaries, ester quaternaries, ethoxylated quaternaries, alkyl amines, and mixtures thereof. The alkyl group preferably comprises in the range from 6 to 30, more preferably 8 to 22, and particularly 10 to 20 carbon atoms. The concentration of cationic surfactant in the composition is preferably in the range from 0 to 20%, more preferably 0.5 to 15%, particularly 1 to 10%, and especially 2 to 8% by weight based on the total weight of the composition.

In the compositions of the present invention, and in particular in hair care compositions, the protein-acrylate copolymers described herein are generally used with one or more of the standard ingredients or carriers. Said standard ingredients or carriers may be selected from any of shine enhancers, moisturisers, herbal additives, hair strengtheners, vitamin additives, colorants, hair thickening agents, setting and styling agents, dandruff control agents, ultraviolet absorbers, silicone oils, essential oils and fragrances, anionic, non-ionic or cationic surfactants, thickening or viscosity-enhancing agents, detergents, stabilising agents, emollients, chelating agents, sequestering agents, preservatives, disinfectants, antioxidants, antistatic agents, conditioning agents, detangling ingredients, emulsifying or dispersing agents, stimulants, soothers, solvents, carriers, and the like, or any combination thereof.

In particular, the composition may comprise a silicone fluid or oil such as dim ethylpolysiloxane, dimethyl silicone, highly polymerised methyl polysiloxane, methyl polysiloxane, polydimethyl siloxane (known generically as dimethicone), cyclic oligomeric dialkylsiloxanes, such as the cyclic oligomers of dimethylsiloxane, (known generically as cyclomethicone). The concentration of silicone oil in the composition is preferably in the range from 0.5 to 50%, more preferably 3 to 30%, particularly 4 to 20%, and especially 5 to 10% by weight based on the total weight of the composition.

The composition, preferably for hair care, may be in the form of an aqueous "leave on" or an aqueous "rinse off" end-use product. For such compositions, a dilute solution of the copolymer in water may be used. The concentration of protein-acrylate copolymer in such a solution is preferably in the range from 0.01 to 5%, more preferably 0.1 to 2%, particularly 0.2 to 1%, and especially 0.4 to 0.5% by weight based on the total weight of the composition. Preferably, a buffered solution is used, in which the pH of the solution is adjusted to mildly acidic, with a pH in the range of from 4 to 6. In the case of rinse-off formulations, instructions are provided to wash off the protein-acrylate copolymer solution after application. Depending on the level of treatment required, such instructions may also require the solution to remain on the hair for some time, such as from 1 to 30 minutes. For leave-on formulations, the washing off step is omitted.

One preferred hair care product is a hair conditioner, which functions to make the hair more shiny and manageable. The conditioner may be in the form of a dispersion, emulsion, or solution. A particularly preferred system is one that forms liquid crystals. The liquid crystals are preferably lyotropic liquid crystals (i.e. both concentration and temperature dependant), more preferably lamellar phase liquid crystals, and particularly L alpha phase (neat) liquid crystals. The concentration of protein-acrylate copolymer in the conditioner is preferably in the range from 0.1 to 10%, more preferably 0.3 to 2%, particularly 0.4 to 1.5%, and especially 0.5 to 1% by weight based on the total weight of the composition.

The conditioner may contain one or more different types of functional ingredients as detailed below;

(i) cationic hair conditioning agents, e.g. ethoxylated phosphate fatty quats, such as that sold by Croda as Crodafos™ CES; fatty amido amines, such as that sold by Croda as Incromine™ SD (stearamidopropyl dimethylamine); fatty quats, such as those sold by Croda as Incroquat™; Polyquaternium-7, such as that sold by Croda as Optasense™ CP7; quaternised proteins, such as those sold by Croda, e.g Hydrotriticum™ QS—the conditioning agents are typically used at a concentration in the range from 1 to 5% by weight based on the total weight of the composition;

(ii) fatty alcohols e.g stearyl, cetearyl, cetyl, oleyl alcohols, used typically at a concentration range of 2 to 5% by weight based on the total weight of the composition;

(iii) humectants or solvents, e.g. alcohols and polyols such as glycerol and polyethylene glycols—used typically at a concentration in the range from 1 to 10% by weight based on the total weight of the composition;

(iv) reconstructors, e.g. hydrolysed proteins such as wheat protein, which function to penetrate the hair and strengthen the hair structure through polymer crosslinking;

(v) glossing or detangling materials which bind to the hair and reflect light, e.g. silicones such as dimethicone, cyclomethicone, phenyltrimethicone, dimethiconal, and/or trimethylsilylamodimethicone—usually at a concentration in the range from 0.5 to 10% by weight based on the total weight of the composition;

(vi) acidity regulators, e.g. citric acid, lactic acid, which generally maintain the pH of the conditioner at about 4 to 6; and (vii) thermal protectors, usually heat-absorbing polymers, which shield the hair against excessive heat, e.g. caused by blow-drying or curling irons or hot rollers In one embodiment, the composition of the invention is in the form of an emulsion (or dispersion), such as an oil-in-water or water-in-oil emulsion, particularly an oil-in-water emulsion.

The oil phase of the emulsion will preferably mainly be an emollient oil of the type used in personal care or cosmetic products. The emollient can, and usually will, be an oily material which is preferably liquid at ambient temperature. Alternatively, it can be solid at ambient temperature, in which case in bulk it will usually be a waxy solid, provided it is liquid at an elevated temperature at which it can be included in and emulsified in the composition.

Suitable normally liquid emollient oils include non-polar oils, for example mineral or paraffin, especially isoparaffin, oils, such as that sold by Croda as Arlamol™ HD; or medium polarity oils, for example vegetable ester oils such as jojoba oil, vegetable glyceride oils, animal glyceride oils, such as that sold by Croda as Estol™ 3603 (caprylic/capric triglyceride), synthetic oils, for example synthetic ester oils, such as isopropyl palmitate and those sold by Croda as Estol™ 1512 and Arlamol™ DOA, ether oils, particularly of two fatty e.g. $C_8$ to $C_{18}$ alkyl residues, such as that sold by Cognis as Cetiol OE (dicaprylether), guerbet alcohols such as that sold by Cognis as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Croda as Arlamol™ E (propoxylated stearyl alcohol).

The concentration of the oil phase may vary widely. The amount of the oil phase in the emulsion is preferably in the range from 1 to 90%, more preferably 2 to 70%, particularly 3 to 50%, and especially 5 to 35%, by weight based on the total weight of the emulsion.

The amount of the aqueous phase in the emulsion is preferably in the range from 10 to 99%, more preferably 30 to 98%, particularly 50 to 97%, and especially 65 to 95%, by weight based on the total weight of the emulsion.

A wide range of emulsifiers may be employed, particularly one or more non-ionic emulsifier(s). Suitable emulsifiers include conventional non-ionic oil-in-water emulsifier surfactants such as alkoxylate emulsifiers, and surfactants that can be derived from natural materials such as fatty acid esters, ethers, hemi-acetals or acetals of polyhydroxylic compounds, or a fatty acid amide which is N-substituted with the residue of a polyhydroxylic compound. The specific nature of the emulsifier surfactant used in any particular instance depends on the type of emulsion being made, particularly the amount and nature of the oil being emulsified and the total desired level of emulsifier.

The concentration of emulsifier in the emulsion is preferably in the range from 0.1 to 20%, more preferably 0.5 to 15%, particularly 1 to 10%, and especially 2 to 7%, by weight based on the total weight of the emulsion.

The protein-acrylate copolymer is preferably present in the aqueous phase of an emulsion according to the present invention. Thus, the aqueous phase of an emulsion suitably comprises in the range from 0.01 to 10%, preferably 0.5 to 5%, more preferably 0.1 to 4%, particularly 0.2 to 2%, and especially 0.3 to 1%, by weight of protein-acrylate copolymer based on the total weight of the emulsion.

Many other components normally used in personal care or cosmetic compositions or end-use products may be included in the compositions according to the present invention. These components may be oil soluble, water soluble or non-soluble. Examples of such materials include:

(i) preservatives such as those based on parabens (alkyl esters of 4-hydroxybenzoic acid), phenoxyethanol, substituted ureas and hydantoin derivatives e.g. those sold commercially under the trade names Germaben II Nipaguard BPX and Nipaguard DMDMH, when used usually in a concentration in the range from 0.5 to 2% by weight based on the total weight of the composition;

(ii) perfumes, when used typically at a concentration in the range from 0.1 to 10% more usually up to about 5% and particularly up to about 2%, by weight based on the total weight of the composition;

(iii) humectants or solvents such as alcohols, polyols such as glycerol and polyethylene glycols, when used typically at a concentration in the range from 1 to 10% by weight based on the total weight of the composition;

(iv) alpha hydroxy acids such as glycolic, citric, lactic, malic, tartaric acids and their esters;

(v) self-tanning agents such as dihydroxyacetone;

(vi) antimicrobial, particularly anti-acne components such as salicylic acid;

(vii) vitamins and their precursors including:
 (a) Vitamin A, e.g. as retinyl palmitate and other tretinoin precursor molecules,
 (b) Vitamin B, e.g. as panthenol and its derivatives,
 (c) Vitamin C, e.g. as ascorbic acid and its derivatives,
 (d) Vitamin E, e.g. as tocopheryl acetate, and
 (e) Vitamin F, e.g. as polyunsaturated fatty acid esters such as gamma-linolenic cid esters;

(viii) skin care agents such as ceramides either as natural materials or functional mimics of natural ceramides;

(ix) natural phospholipids, e.g. lecithin;

(x) vesicle-containing formulations;

(xi) botanical extracts with beneficial skin care properties;

(xii) skin whiteners such as dioic acid, kojic acid, arbutin and similar materials;

(xiii) skin repair compounds actives such as Allantoin and similar series;

(xiv) caffeine and similar compounds;

(xv) cooling additives such as menthol or camphor;

(xvi) insect repellents such as N,N-diethyl-3-methylbenzamide (DEET) and citrus or eucalyptus oils;

(xvii) essential oils; and (xviii) pigments, including microfine pigments, particularly oxides and silicates, e.g. iron oxide, particularly coated iron oxides, and/or titanium dioxide, and ceramic materials such as boron nitride, or other solid components, such as are used in make up and cosmetics, to give suspoemulsions, typically used in an amount in the range from 1 to 15%, but usually at least 5% and particularly about 10% by weight based on the total weight of the composition.

In an alternative embodiment, the composition of the present invention may be a home care or an industrial formulation such as a light duty detergent, laundry detergent, hard surface cleaner, industrial cleaner, metal working and lubricating agent, emulsifier, anti-corrosion agent for metal products and various other liquid and/or water based home care, industrial, crop and/or textile compositions.

In order that the present invention may be more readily understood, reference will now be made, by way of example, to the following description.

In this specification the following test methods have been used:

1) Molecular Weight of Protein and Protein-Acrylate Copolymer

Molecular weight (weight average) was determined by size exclusion HPLC using the following methodology.

(i) Protein-Acrylate Copolymer;

Column TSK-GEL GMPWxI (30 cm×7.8 mm internal diameter)

Guard column TSK PWxI (4 cm×6 mm internal diameter)

Pump HP1100 series isocratic pump (G1310A)

Injector HP1100 series autosampler (G1313A)

Thermostat HP1100 series thermostated column compartment (G1316A)
Detector HP1100 series refractive index detector (G1362A)
Control HP1100 series Chemstation software (G2175A)
Integration Polymer Laboratories Cirrus GPC software
Eluent 0.52M sodium acetate and 0.31M glacial acetic acid in water
Flow rate 0.6 ml per minute
Injection volume 5
Temperature 40° C.
Wavelength 220 nm
Standards PEG/PEO standards of known molecular weight. 12 standards were used in the range 106 to 1,215,000 Daltons.
Calibration fit type First order polynomial (linear)
Fit ratio 1.00±0.02
(ii) Protein
As (i) above except that;
Column TSK-GEL G2000SWxI (30 cm×7.8 mm internal diameter)
Guard column TSK SWxI (4 cm×6 mm internal diameter)
Detector HP1100 series variable wavelength detector (G1314A)
Eluent 0.05M $KH_2PO_4$, 0.06M $K_2HPO_4.3H_2O$ and 0.1M NaCl adjusted to pH 7.0
Temperature 25° C.
Standards Protein standards of known molecular weight. 4 standards were used in the range 75 to 67,000 Daltons.
Calibration fit type Cubic splines 2) Hair Volume Enhancement Test (i) Pre-tressed virgin European hair tresses were cut into swatches of 15 mm width.

(ii) The swatch was wetted by quick submersion in water, washed with 1 mL of basic shampoo for 30 seconds, and rinsed with warm tap water for 1 minute.

(iii) The swatch was gently detangled with a wide-teethed comb.

(iv) 0.5 g of basic, active or control conditioner was applied by spraying along the swatch and massaged by hand for 30 seconds.

(v) The swatch was rinsed for a minute with warm tap water.

(vi) The swatch was suspended from the top and allowed to dry naturally over night at room temperature.

(vii) Photographs of the swatch were taken the next morning from the front and the side and analysed using Image-J software to give a figure for the size of the tress.

The basic shampoo formulation contained 35% by weight of Empicol ESB 3 (ex Huntsman), 10% by weight of Crodateric™ CAB 30 (ex Croda), 0.2% by weight of citric acid, and deionised water up to 100% by weight.

The basic conditioner formulation contained 5% by weight of Incroquat™ Behenyl TMS 50 (ex Croda), 5% by weight of Crodacol™ C 90 (ex Croda), 1% by weight of Phenonip (ex Clariant), 0.2% by weight of citric acid, and deionised water up to 100% by weight. The active conditioner formulation additionally contained 1% by weight of the reaction product of Examples 1, 2 or 3 below. The control conditioner formulation was a leading commercially available conditioner.

In order that the present invention may be more readily understood, reference will now be made, by way of example, to the following description.

The invention is illustrated by the following non-limiting examples.

EXAMPLE 1

31.5 g of enzyme hydrolysed wheat protein (20% by weight aqueous solution) having a molecular weight (weight average) of 1,500 Daltons and 62 g of water were mixed in a flange flask. The pH was adjusted to 6.0 by adding 25% by weight of sodium hydroxide solution.

The flange flask was fitted with a lid, stirrer guide, thermometer, condenser and sealed. 31.5 g of N,N,N-trimethylamino ethyl methacrylate (DMAEMA-MC) (Ageflex FM1Q 80MC, ex Ciba) (80% by weight aqueous solution) was added to the flask from a beaker. The beaker was rinsed with 45 g of water, which was also added to the flask. The flask was then transferred to a water bath where it was heated to 60° C. with stirring. A solution of 1.18 g of V50 initiator (azobis(amidinopropane)dihydrochloride) in 11.8 g of water was prepared, and added to the flask in even portions (approximately every 12 minutes) over 2 hours.

Once the addition was complete, the temperature was increased to 80° C. and the reaction was allowed to proceed for a further 5 hours with stirring. The temperature was allowed to cool below 30° C., and the pH adjusted to 4.0 to 5.0 with 28% by weight of hydrochloric acid. 0.3% w/w phenoxytol, 0.2% w/w potassium sorbate and 0.2% w/w disodium EDTA were added. The pH was again adjusted to 4.0 to 5.0, if necessary. The resulting liquor was filtered to give a clear yellow aqueous solution reaction product containing approximately 20% by weight of total solids (excluding salt) having a molecular weight (weight average) of 43K Daltons (obtained by integrating all of peaks present in the chromatogram, including those of any residual starting materials). The protein-acrylate copolymer had a molecular weight (weight average) of 108K Daltons (obtained by only integrating the high molecular weight peak in the chromatogram).

The reaction product was evaluated in the hair volume enhancement test described herein, and the hair volume results were as follows;
i) Basic Conditioner=63.8 area units,
ii) Active Conditioner=82.2 area units, and
iii) Control Conditioner=83.0 area units.

In addition, the active conditioner containing the protein-acrylate copolymer gave good feel to the hair, with little or no frizz or fly-away of the hair.

EXAMPLE 2

The procedure of Example 1 was repeated except that 15.8 g of DMAEMA-MC were used, and the resulting aqueous solution had a molecular weight (weight average) of 21.5K Daltons. The protein-acrylate copolymer had a molecular weight (weight average) of 88K Daltons.

The reaction product was evaluated as in Example 1 and the hair volume result was as follows;
i) Active Conditioner=82.6 area units

EXAMPLE 3

The procedure of Example 1 was repeated except that 63.0 g of DMAEMA-MC were used, and the resulting aqueous solution had a molecular weight (weight average) of 59K Daltons. The protein-acrylate copolymer had a molecular weight (weight average) of 137K Daltons.

The reaction product was evaluated as in Example 1 and the hair volume result was as follows;
i) Active Conditioner=84.4 area units.

EXAMPLE 4

The reaction product of Example 1 was used to prepare a volumising conditioner having the following composition;

| Product/INCI Name | Functionality | % w/w |
|---|---|---|
| CRODACOL ™ S95 (Stearyl alcohol)[1] | Viscosity builder | 1.0 |
| COSMOWAX ™ J (Cetearyl Alcohol (and) Steareth-20 (and) Steareth-10)[1] | Emulsifier | 4.0 |
| INCROMINE ™ SD (Steariamidopropyl Diethylamine)[1] | Conditioner | 2.0 |
| Protein-Acrylate Copolymer Solution Produced in Example 1 | Volumising active | 5.0 |
| CROPEPTIDE ™ W (Aqua (and) Hydrolysed Wheat Protein (and) Hydrolysed Wheat Starch)[1] | Moisture regulating active | 1.0 |
| Fragrance Tresses (Fragrance)[2] | Fragrance | 5.0 |
| Euxyl K300 (Phenoxyethanol (and) Methylparaben (and) Butylparaben (and) Ethylparaben (and) Propylparaben (and) Isobutylparaben)[3] | Preservative | 0.8 |
| Citric acid (10% solution) | pH adjuster | To pH 4-4.5 |
| Water Deionised (Aqua) | | To 100 |

Suppliers: [1] roda, [2] Ungerer, and [3] Schulke

Procedure

The oil phase ingredients (viscosity builder, emulsifier and conditioner) were combined and heated to 75-80° C. The water phase was heated to 75-80° C. The water was added to the oil phase with stirring. The mixture was cooled to room temperature with stirring, whilst adding the remaining ingredients below 40° C. The pH was adjusted to 4-4.5 with citric acid. The resulting product was a white cream having a pH of 4.95 and viscosity of 23,000 mPa·s (Brookfield RVDV1, spindle C, 10 rpm, 1 minute).

The volumising conditioner was evaluated in salon studies, and the trained assessors reported a statistically significant increase in hair volume.

EXAMPLE 5

The reaction product of Example 1 was used to prepare a volumising spritz having the following composition;

| Product/INCI Name | Functionality | % w/w |
|---|---|---|
| CRODASOL ™ AC (PEG-6 Caprylic/Capric Glycerides (and) PEG-60 Almond Glycerides)[1] | Solubiliser | 5.0 |
| Fragrance Tresses (Fragrance)[2] | Fragrance | 0.5 |
| INCROMECTANT ™ LAMEA (Acetamide MEA (and) Lactamide MEA)[1] | Humectant | 5.0 |
| Protein-Acrylate Copolymer Solution Produced in Example 1 | Volumising active | 2.5 |
| CROTEIN ™ CAA S/F (Aqua (and) Collagen Amino Acids)[1] | Hair moisturising active | 1.0 |
| Euxyl K300 (Phenoxyethanol (and) Methylparaben (and) Butylparaben (and) Ethylparaben (and) Propylparaben (and) Isobutylparaben)[3] | Preservative | 0.5 |
| Water Deionised (Aqua) | | To 100 |

Suppliers: [1] Croda, [2] Ungerer, and [3] Schulke

Procedure

The fragrance, solubiliser and humectant were combined and added to water with stirring.

The remaining ingredients were added with stirring. The resulting product was a water thin clear pale yellow liquid.

The above examples illustrate the improved properties of a protein-acrylate copolymer and composition according to the present invention.

It is to be understood that the invention is not to be limited to the details of the above embodiments, which are described by way of example only. Many variations are possible.

The invention claimed is:

1. A protein-acrylate copolymer comprising at least one nitrogen containing acrylic monomer;
wherein:
   i) the protein of the protein-acrylate copolymer is a hydrolyzed protein of 8 to 50 amino acids; and
   ii) the nitrogen containing acrylic monomer comprises at least 60 mol. % of monomers comprising tertiary and/or quarternary amine groups.

2. A protein-acrylate copolymer obtainable by reacting a protein component with an acrylate component comprising at least one nitrogen containing acrylic monomer;
wherein:
   i) the protein of the protein-acrylate copolymer is a hydrolyzed protein of 8 to 50 amino acids; and
   ii) the nitrogen containing acrylic monomer comprises at least 60 mol. % of monomers comprising tertiary and/or quarternary amine groups.

3. The copolymer according to claim 1, wherein the nitrogen containing acrylic monomer comprises a tertiary or quaternary amine group.

4. The copolymer according to claim 3, wherein the nitrogen containing acrylic monomer comprises a quaternary amine group.

5. The copolymer according to claim 4, wherein the nitrogen containing acrylic monomer comprises at least 40 mole % of monomers comprising a quaternary amine group.

6. The copolymer according to claim 1, wherein the copolymer has a molecular weight (weight average) in the range from 20,000 to 500,000 Daltons.

7. The copolymer according to claim 1, wherein the molecular weight (weight average) of the protein is in the range from 500 to 10,000 Daltons.

8. The copolymer according to claim 1, wherein the ratio of protein to acrylate is in the range from 20%:80% to 80%:20% by weight.

9. A composition comprising in the range from 0.01 to 20% by weight of a protein-acrylate copolymer, said copolymer comprising at least one nitrogen containing acrylic monomer;
wherein:
   i) the protein of the protein-acrylate copolymer is a hydrolyzed protein of 8 to 50 amino acids; and
   ii) the nitrogen containing acrylic monomer comprises at least 60 mol. % of monomers comprising tertiary and/or quarternary amine groups.

10. The composition according to claim 9, wherein the composition is a personal care or cosmetic product.

11. The composition according to claim 9, wherein the composition is a hair care or skin care product.

12. The composition according to claim 9, wherein the composition is a hair conditioning product.

13. A method of producing a protein-acrylate copolymer which comprises reacting protein with at least one nitrogen containing acrylic monomer, and/or oligomer and/or polymer formed from at least one nitrogen containing acrylic monomer;

wherein:
i) the protein of the protein-acrylate copolymer is a hydrolyzed protein of 8 to 50 amino acids; and
ii) the nitrogen containing acrylic monomer comprises at least 60 mol. % of monomers comprising tertiary and/or quarternary amine groups.

14. The method of claim 13, wherein at least one nitrogen containing acrylic monomer is reacted with the protein.

15. A method of treating hair, comprising: applying a composition comprising the protein-acrylate copolymer of claim 1.

16. A method of increasing the volume of hair comprising applying a composition comprising the protein-acrylate copolymer of claim 1.

17. The copolymer according to claim 1, wherein the protein-acrylate copolymer is a random copolymer, a graft copolymer, or a block copolymer.

18. The copolymer according to claim 17, wherein the protein-acrylate copolymer is a graft copolymer.

19. The composition according to claim 9, wherein the protein-acrylate copolymer is a random copolymer, a graft copolymer, or a block copolymer.

20. The method according to claim 13, wherein the produced protein-acrylate copolymer is a random copolymer, a graft copolymer, or a block copolymer.

* * * * *